(12) United States Patent
Kaye et al.

(10) Patent No.: US 8,088,079 B2
(45) Date of Patent: Jan. 3, 2012

(54) POLYP TRAP

(75) Inventors: Christopher J. Kaye, Concord, OH (US); K. Randall John, Chardon, OH (US); Dean J. Secrest, Concord, OH (US); Colleen Quinn, South Euclid, OH (US)

(73) Assignee: U.S. Endoscopy Group, Inc., Mentor, OH (US)

( * ) Notice: Subject to any disclaimer, the term of this patent is extended or adjusted under 35 U.S.C. 154(b) by 379 days.

(21) Appl. No.: 11/705,291

(22) Filed: Feb. 12, 2007

(65) Prior Publication Data

US 2007/0191731 A1    Aug. 16, 2007

Related U.S. Application Data

(60) Provisional application No. 60/772,330, filed on Feb. 10, 2006.

(51) Int. Cl.
*A61B 10/00* (2006.01)
(52) U.S. Cl. .................................. 600/562; 210/767
(58) Field of Classification Search ............ 604/37; 600/562
See application file for complete search history.

(56) References Cited

U.S. PATENT DOCUMENTS

| 4,376,053 | A | * | 3/1983 | Bullock et al. ............ 210/767 |
| 4,439,319 | A | | 3/1984 | Rock |
| 4,643,197 | A | | 2/1987 | Greene et al. |
| 4,852,560 | A | | 8/1989 | Hermann, Jr. et al. |
| 4,870,975 | A | | 10/1989 | Cronk et al. |
| 4,957,492 | A | | 9/1990 | McVay |
| 5,027,827 | A | | 7/1991 | Cody et al. |
| 5,049,273 | A | | 9/1991 | Knox |
| 5,108,381 | A | | 4/1992 | Kolozsi |
| 5,223,151 | A | * | 6/1993 | Rojas ............................ 210/767 |
| 5,256,160 | A | | 10/1993 | Clement |
| 5,347,991 | A | | 9/1994 | Nakao et al. |
| 5,363,860 | A | | 11/1994 | Nakao et al. |
| 5,383,234 | A | * | 1/1995 | Russell ......................... 378/164 |
| 5,575,293 | A | | 11/1996 | Miller et al. |
| 5,624,418 | A | | 4/1997 | Shepard |
| 5,797,742 | A | * | 8/1998 | Fraker ............................ 433/92 |

(Continued)

FOREIGN PATENT DOCUMENTS

WO    WO/2004/075740    *    9/2004

OTHER PUBLICATIONS

Article Photograph of Suction Polyp Trap by EndoDynamics, Inc., Gastroenterology & Endoscopy News, dated Unknown.

(Continued)

*Primary Examiner* — Max Hindenburg
*Assistant Examiner* — Renee Danega
(74) *Attorney, Agent, or Firm* — Calfee, Halter & Griswold LLP

(57) ABSTRACT

A polyp trap for use in collecting tissue samples. The device includes a collection container and a removable tray. The collection container has an inlet port, a sidewall aperture, and an exit port. The removable tray has a first end and a second end. The tray is sized for movement within the sidewall aperture between an inserted position forming a seal with the collection container and a withdrawn position remote from the collection container. The tray has a perforated bottom surface such that fluids traveling under suction from the inlet port to the outlet port pass through the tray.

18 Claims, 6 Drawing Sheets

U.S. PATENT DOCUMENTS

| | | | |
|---|---|---|---|
| 5,817,032 | A | 10/1998 | Williamson, IV et al. |
| 5,928,935 | A * | 7/1999 | Reuss et al. ............... 435/288.1 |
| 6,375,625 | B1 | 4/2002 | French et al. |
| 6,562,233 | B1 * | 5/2003 | Schilling et al. ............ 210/164 |
| 6,572,578 | B1 | 6/2003 | Blanchard |
| 6,695,791 | B2 | 2/2004 | Gonzalez |
| 6,749,319 | B1 * | 6/2004 | Muse ............................ 362/154 |
| 6,835,198 | B2 | 12/2004 | Bonutti |
| 7,294,256 | B2 * | 11/2007 | Happel et al. ................ 210/155 |
| 2003/0125639 | A1 * | 7/2003 | Fisher et al. .................. 600/564 |
| 2004/0230135 | A1 | 11/2004 | Merkle |
| 2004/0242960 | A1 | 12/2004 | Orban, III |
| 2005/0038374 | A1 | 2/2005 | Williams, Jr. et al. |
| 2006/0231508 | A1 * | 10/2006 | Marzett et al. ............... 210/767 |

OTHER PUBLICATIONS

Environ-Mate PT 20 Trap by MD Technologies, Inc.; EndoNurse Dec. 2002/Jan. 2003, pp. 12.

Website page; EZ-EM Inc., Top Products—Features and Benefit Four Capture Chambers; http://www.ezem.com.gastroenterology/suction.asp?action-gastroenterology.

Website page; of EZ-EM Inc., Top Products—Features and Benefit; Four Capture Chambers; http://www.ezem.com.gastroenterology/suction.asp?action-gastroenterology.

Website page; of EZ-EM Inc., Top Products—Features and Benefit; Lab Transport Device; http://www.ezem.com.gastroenterology/suction.asp?action-gastroenterology.

Website page; of EZ-EM Inc., Top Products—Features and Benefit; Eas in-Line Installation; http://www.ezem.com.gastroenterology/suction.asp?action-gastroenterology.

Website page; of EZ-EM Inc., Top Products—Features and Benefit; Removable Top; http://www.ezem.com.gastroenterology/suction.asp?action-gastroenterology.

Cost-Cutting Concepts for Endoscopy; Endobasic Polyp Traps; website page; http://basic.com/cgibin/quikstore.cgi?p.=polyptrap.ht.

Specimen Collectors, Traps, website page; www.mdtechnologiesinc.com/productsCat23508.ct.

* cited by examiner

POLYP TRAP

CROSS-REFERENCE TO RELATED APPLICATIONS

This non-provisional application claims the benefit of U.S. Provisional Patent Application No. 60/772,330, entitled "Polyp Trap," filed Feb. 10, 2006, the entire disclosure of which is incorporated herein by reference, to the extent that it is not conflicting with this application.

FIELD OF THE INVENTION

The present invention relates to a polyp trap and to a polyp trap for use in capturing a polyp removed during an endoscopic procedure.

BACKGROUND OF THE INVENTION

Physicians routinely perform procedures to remove and recover tissue samples from a patient for a variety of reasons. One such procedure is the removal and recovery of a polyp from the gastrointestinal wall of a patient. In an exemplary procedure, an endoscope is used in the removal and recover of the polyp. An endoscope is inserted through a patient's esophagus to begin a typical procedure. The endoscope is flexible and typically has optical and illuminating features. In such a procedure, after a polyp is cut or otherwise detached from the gastrointestinal wall, the polyp is either mechanically recovered by a snare or removed by suction.

Prior art solutions for polyp recovery have many limitations. Recovery by snare is time consuming and limits the amount of polyps that can be recovered without endoscope removal. Recover by suction requires a physician, nurse or technician to monitor a location between the endoscope exit port and the suction source to recover the polyp. At such a location, a polyp trap can be used. Prior art polyp traps have been complicated in design, expensive, or difficult to use.

There remains a need in the art for a polyp trap that is easy to operate, allows for multiple polyp recovery during a single intubation, and is inexpensive enough to warrant one-time use.

SUMMARY OF THE INVENTION

In several illustrated embodiments of the present invention, a polyp trap for capturing a polyp removed during an endoscopic procedure is disclosed. The polyp trap includes a collection container and a removable tray. When assembled, the removable tray forms a seal with the collection container to allow a suction to be pulled through inlet and outlet ports of the collection container.

Further features and advantages of the invention will become apparent from the following detailed description made with reference to the accompanying drawings.

DETAILED DESCRIPTION OF THE INVENTION

This Detailed Description of the Invention merely describes embodiments of the invention and is not intended to limit the scope of the claims in any way. Indeed, the invention as described is broader than and unlimited by the preferred embodiments, and the terms used have their full ordinary meaning.

During an endoscopic procedure, a physician often locates tissue that is identified as polyps or other abnormal tissue growth on the gastrointestinal wall of a patient. Analysis of such polyps can be beneficial for diagnostic reasons. Polyps may be removed from the gastrointestinal wall by use of a variety of cutting techniques. After severing the polyp, the tissue may be suctioned out of the body through an endoscope instrument channel. A polyp trap is a device known in the art that is disposed downstream from the endoscope to capture a removed polyp.

Figure 1:
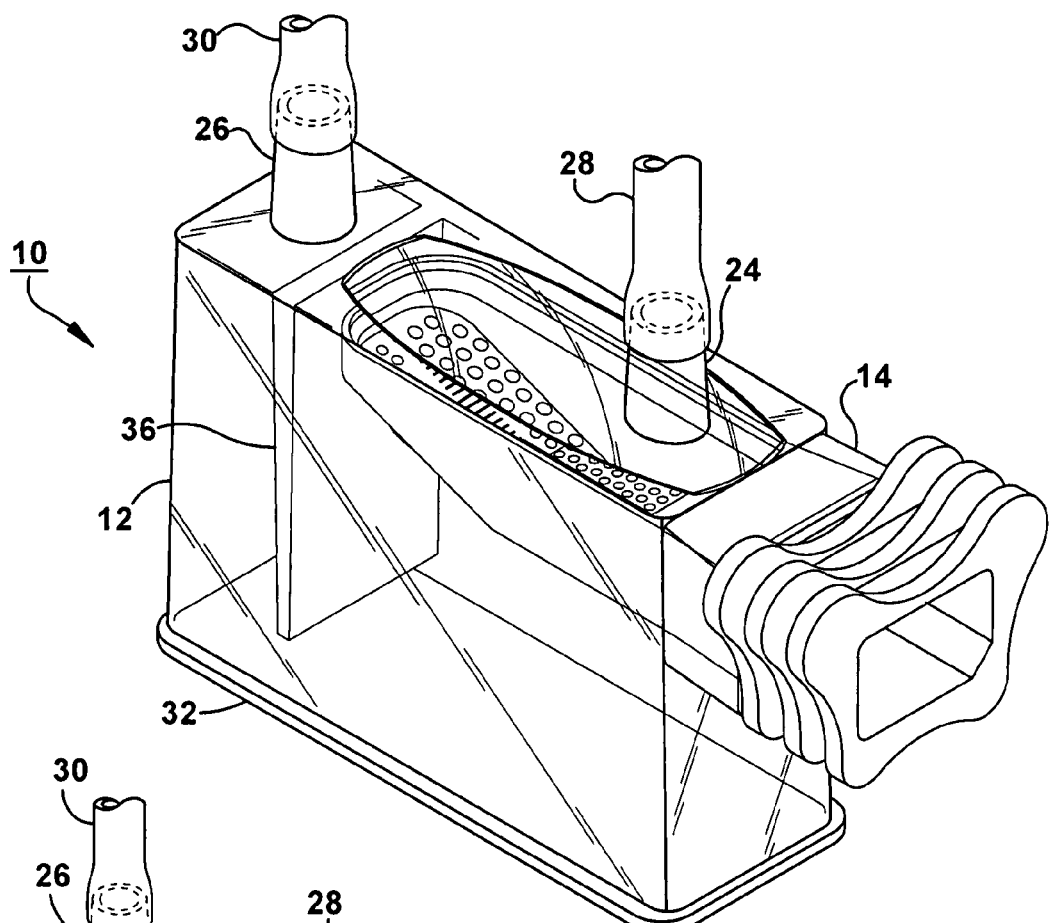
FIG. 1 is a perspective view of a polyp trap made in accordance with an embodiment of the invention, showing a polyp trap having a collection container and a removable tray, with the removable tray in an installed position.
Figure 2:
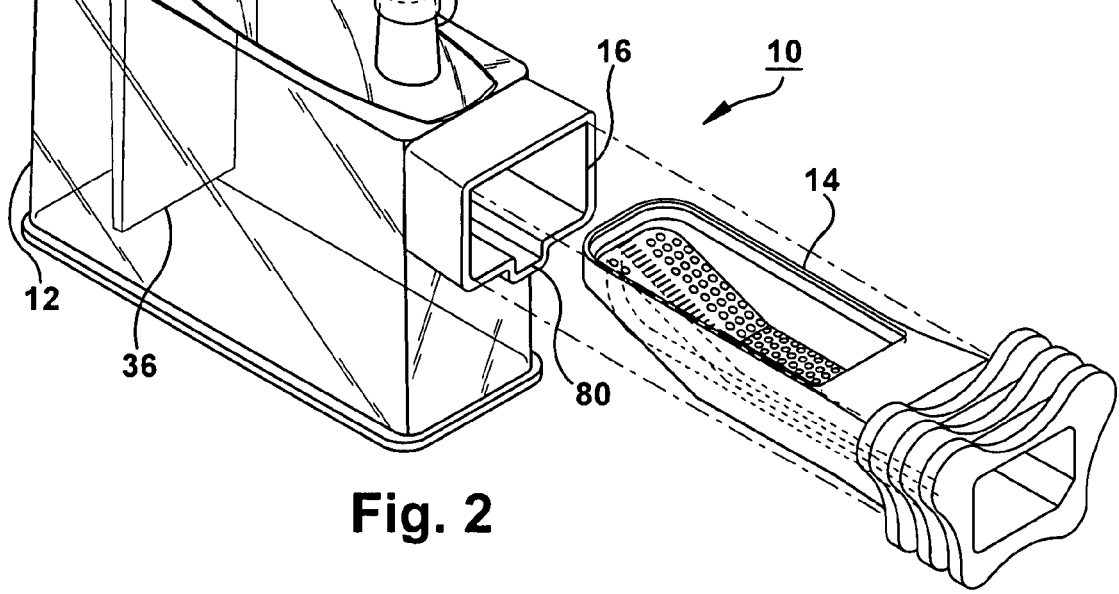
FIG. 2 is a perspective view of the polyp trap of FIG. 1, showing the removable tray in a fully withdrawn position.
Figure 12:
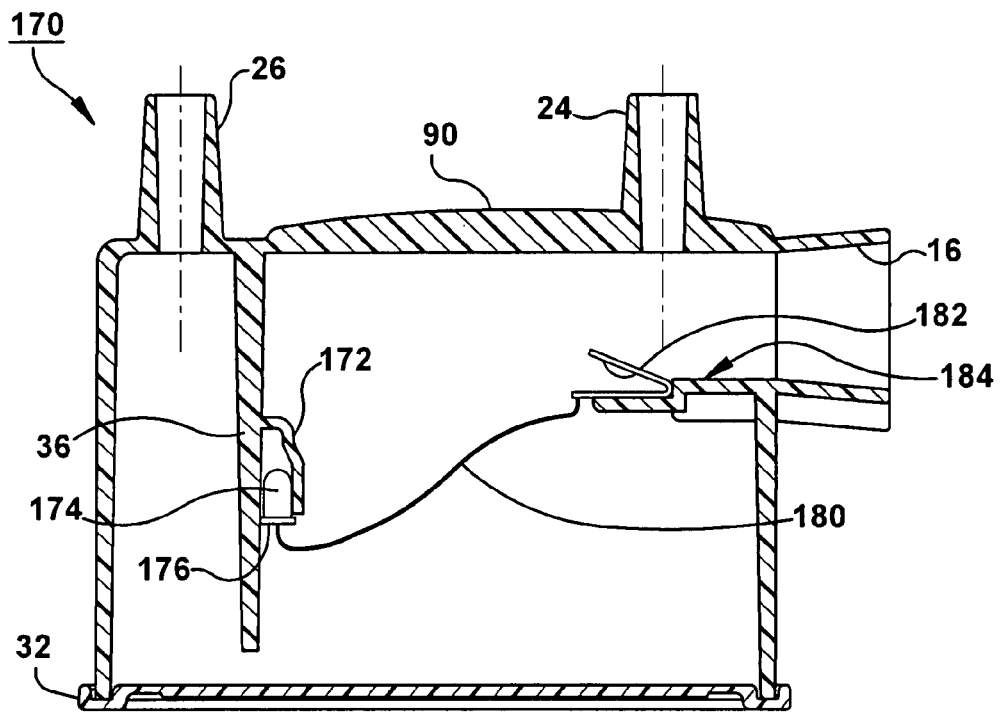
FIG. 12 is a cross-sectional view of yet another embodiment of the present invention, showing a polyp trap having a light source and internal electrical components.

Referring now to the drawings, FIGS. 1 and 2 are perspective views of a polyp trap 10 including a collection container 12 and a removable tray 14. FIG. 1 shows the assembled polyp trap 10 with the tray 14 slide into an aperture 16 in the collection container 12 to a fully inserted position. As best seen in FIG. 12, the aperture passage narrows in width and height toward the inside of the collection container 12. When slid fully into an assembled position, the removable tray 14 forms a seal with the collection container 12. FIG. 2 shows the removable tray 14 fully withdrawn from the collection container 12.

The collection container 12 is a six-sided hollow object that may be constructed of clear plastic or otherwise transparent material. The collection container 12 has two ports 24, 26 through a top surface. The protruding ports are conical shaped and narrow in outer diameter toward a distal end to facilitate the press-on application of tubing. Polyps, blood, and other fluids enter the collection container 12 from an endoscope (not shown) through a tube 28 attached to the inlet port 24. A portion of this material under suction exits the collection container 12 through the outlet port 26 and into a tube 30 towards a suction source (not shown). A certain amount of material will remain at the bottom of the container below the tray.

Figure 8:
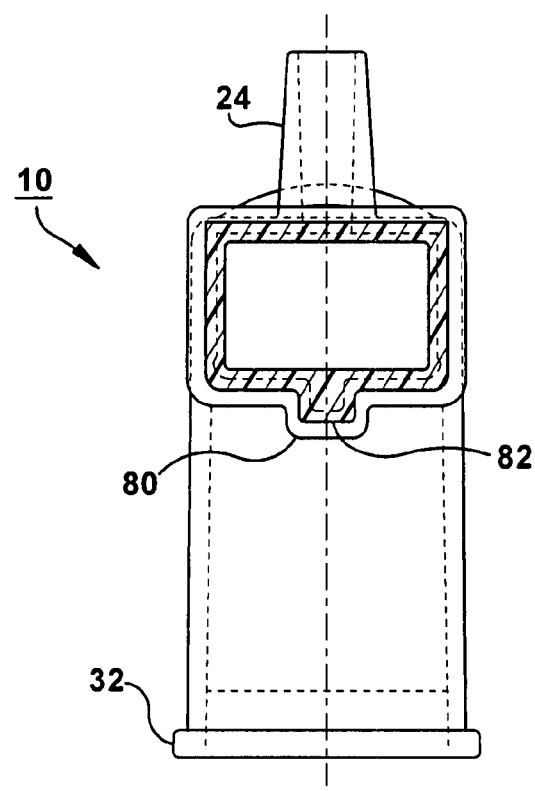
FIG. 8 is a cross-sectional view of the polyp trap of FIG. 1, as seen along the lines 8-8 of FIG. 7.

The collection container 12 includes a base rim 32, as best seen in FIGS. 8 and 12. The rim footprint is larger in size than the collection container main body at its largest point. As such, the collection container 12 will rest upright on a horizontal surface and provides favorable user ergonomics. The base may be integral with the collection container body or a separate piece, such as shown in FIG. 12, and fixed to the main body by adhesive or any other suitable technique.

Figure 6:
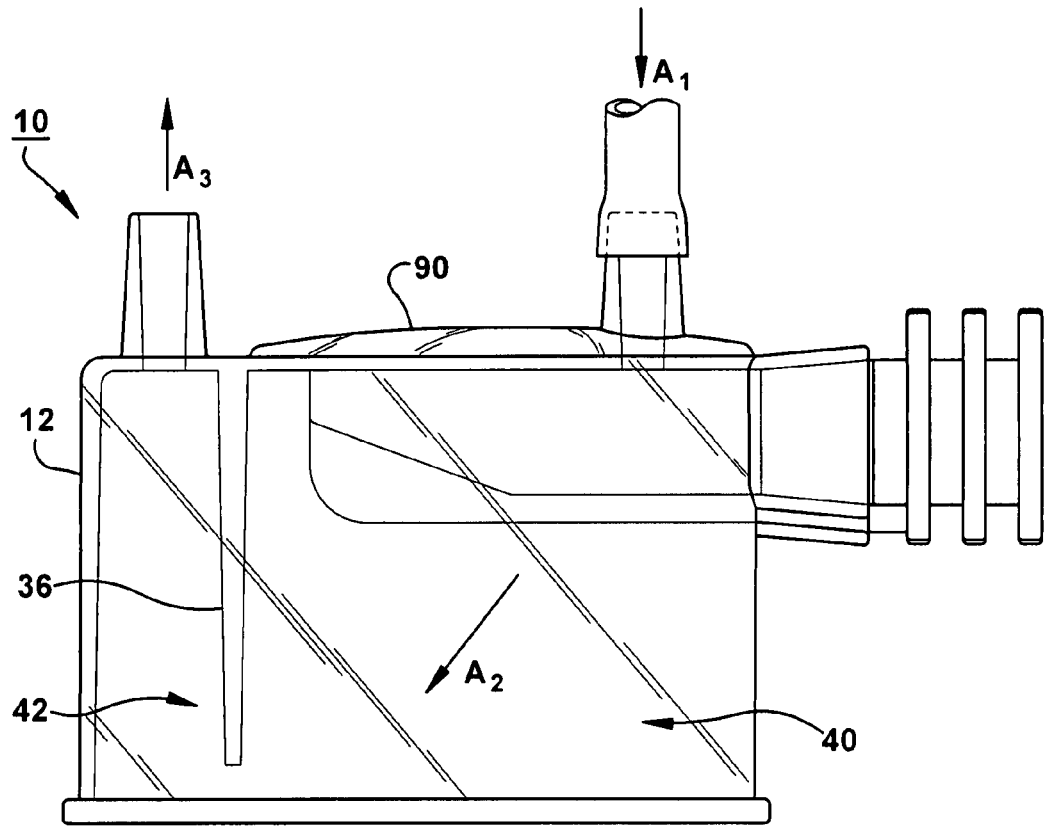
FIG. 6 is a side elevation view of the polyp trap of FIG. 1.

The size and shape of the collection container 12 is designed to optimize performance. Specifically, the container 12 has an optimal volume to ensure suctioned liquid does not accumulate to a level to float the polyp off of the tray surface. Other prior art designs are susceptible to creating a liquid volume buildup that is excessive. Further, the outlet port 26 is remote from the polyp tray and inlet port 24, prohibiting a polyp from being suctioned out of the collection container. As best seen in FIG. 6, a vertically descending dam 36 divides the container into an inlet volume portion 40 and an outlet volume portion 42. Such structure is believed to further prohibit a polyp from being suctioned out of the collection container 12 and increase fluid flow through the container. Travel of blood and other fluids follows the general direction of $A_1$, $A_2$ and $A_3$ through the polyp trap 10 of FIG. 6, as somewhat directed by the dam 36.

It should be understood by those with ordinary skill in the art that the size, shape, wall thickness, inlet and outlet port size and shape, and any other structural features of the collection container shown in the Figures is for exemplary purposes only, and that these and other features may vary in the practice of the present invention.

The removable tray 14 is used to capture polyps suctioned through the inlet port 24. The tray 14 may be constructed of any suitable material, such as for example, a polymer that resists sticking of polyp. Further, the tray may be colored to provide a visual contrast to the polyp, as compared to for example, a transparent tray.

Figure 3:
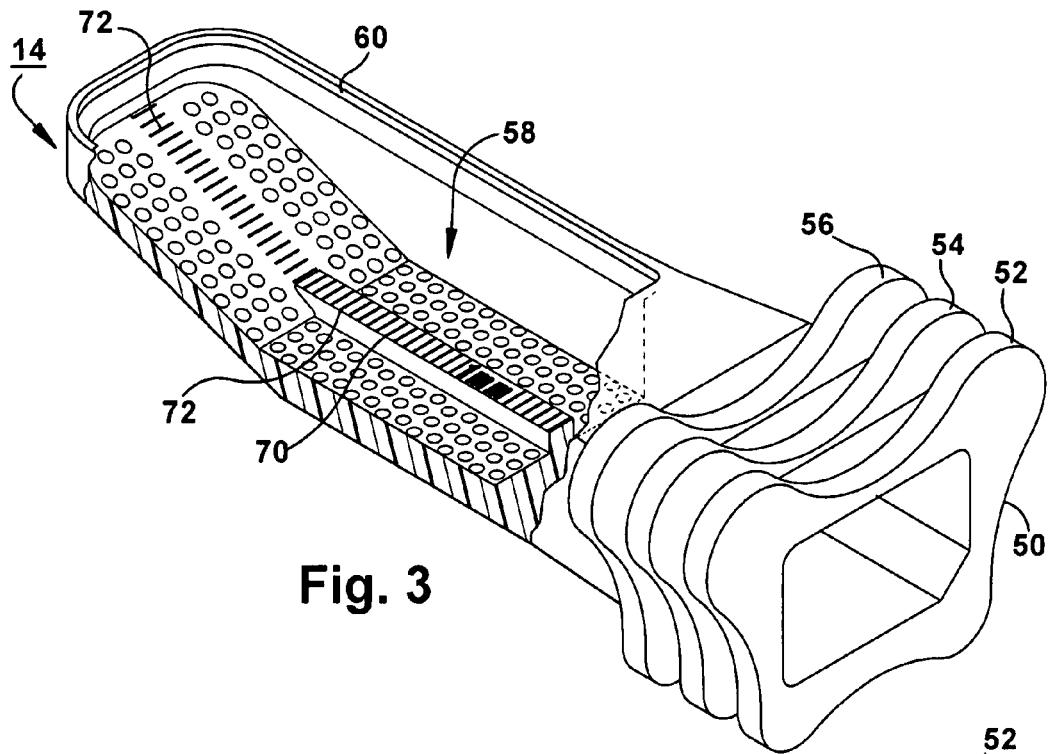
FIG. 3 is a perspective view, partially in section, of the removable tray of FIG. 1.
Figure 4:
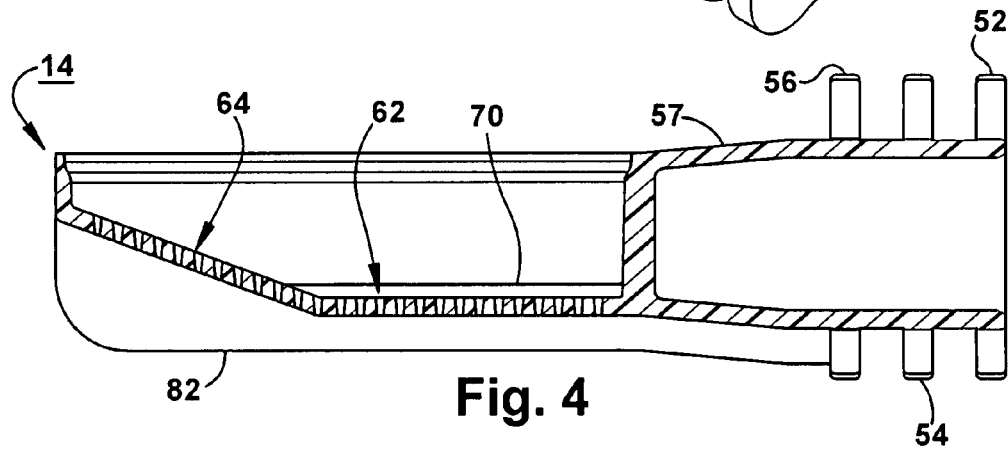
FIG. 4 is a cross-sectional view of the removable tray of FIG. 1.

A perspective view of the removable tray withdrawn from the collection container 12 is shown in FIG. 3. A cross-sectional view of the removable tray 14 is shown in FIG. 4. The tray 14 has a handle 50 located at a proximal end. The handle includes a set of butterfly shaped protruding ridges 52, 54, 56 that an operator may grasp in manipulating the tray 14. This shape also provides a tactile cue so that the tray can be inserted with the proper side up. A connecting portion 57 of narrowing height and width is located distal the handle. Handling of the tray by the handle maintains a sterile center basket 58 of the tray in which a polyp will rest. An outer wall 60 forms the polyp collection basket 58. As shown in FIG. 4, the basket includes an essentially flat bottom surface 62 in the main portion and an inclined bottom surface 64 in a distal portion, relative the handle 50. As seen best in FIGS. 2 and 3, the bottom surface 62, 64 of the removable tray 14 is perforated such that blood and other fluids may pass. Conversely, polyps larger in diameter than a perforation will not pass through the tray 14.

Polyps that enter the collection container 12 and contact the inclined surface 64 are directed toward the flat surface 62 by suction and gravity forces. Once on the flat surface 58, polyps may rest on either side of a longitudinal ridge 70. The ridge 70 includes a series of markings 72 of equal distance, such as for example, 1 mm. A physician may rely on the markings 72 to ascertain the approximate size of the captured polyp. Depending on the desired purposes of the polyp collection, only polyps of a minimum size may be sufficient. The tray may also include dimension indicia in regard to the spacing of the markings. Further, the markings may be located on other portions of the tray, or on the sidewalls of the collection container.

It should be understood by those with ordinary skill in the art that the size, shape, wall thickness, any other structural features of the removable tray shown in the Figures is for exemplary purposes only, and that these and other features may vary in the practice of the present invention.

At the beginning of an endoscopic procedure using the polyp trap 10, the removable tray 14 is inserted into the collection container 12 through the aperture 16 in a vertical sidewall of the collection container 12. In this position, a seal is formed between the contain 12 and the tray 14. As best seen in FIG. 8, the aperture 16 includes a bottom trough 80 sized to guide a longitudinal center ridge 82 on the bottom surface of the removable tray 14 during insertion and removal. The trough 80 extends inward and outward from a sidewall of the collection container 12. The trough eases insertion and prevents attempts to insert at a 90 degree or 180 degree angle. As mentioned, an operator may use a finger grip handle 50 to hold the removable tray 14 during insertion or removal. Compressing on the finger grip handle 50 will break the seal between the removable tray 14 and collection container 12, which will aid in removal.

Figure 7:
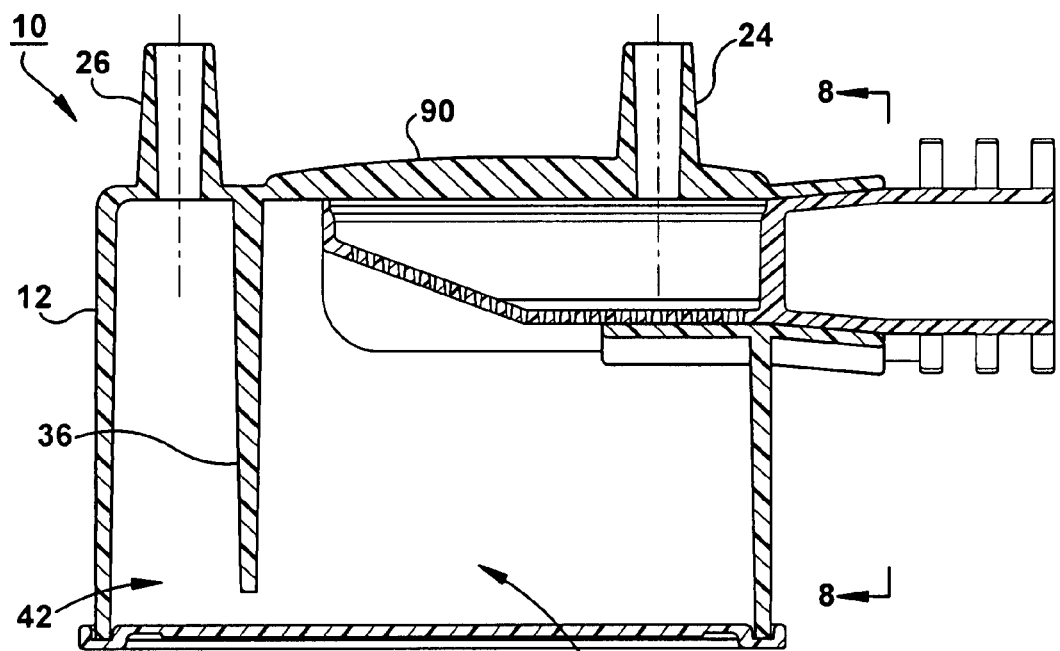
FIG. 7 is a cross-sectional view of the polyp trap of FIG. 1.

Three additional views of the removable tray in an installed position are shown in FIGS. 6-8. As mentioned, the tray includes surfaces 62, 64 of perforations to allow blood and other fluids to pass under suction. A polyp of any significant diameter will be trapped in the removable tray 12. To improve visual recognition of captured material, a user may view the polyp through a magnifying portion 90 of the collection container 12 to study the captured polyp. As such, a user can verify the targeted polyp has been recovered, ascertain the approximate size of the polyp, determine the number of polyps disposed on the upstream surfaces 62, 64 of the tray, or study the polyp for any other diagnostic reasons.

Once identified, the suction source may be turned off and the removable tray 12 may be removed by hand. However, removing the tray will break the system suction, so it is not necessary to turn the suction source off prior to removing the tray. Regardless, the seal fit of the tray to the container advantageously creates a wiper affect during withdrawal of the tray. Consequently, the polyp does not stick to the container but is forced downward into the tray. No other mechanical steps for removal are required. The design affords the user quick and easy access to a captured polyps. The tray can then be held into a formalin jar so that the captured polyp can be rinsed off the tray. If multiple polyp samples are required, a second tray can be used to allow the endoscopic procedure to proceed without interruption while the polyp is removed from the first tray.

Figure 5:
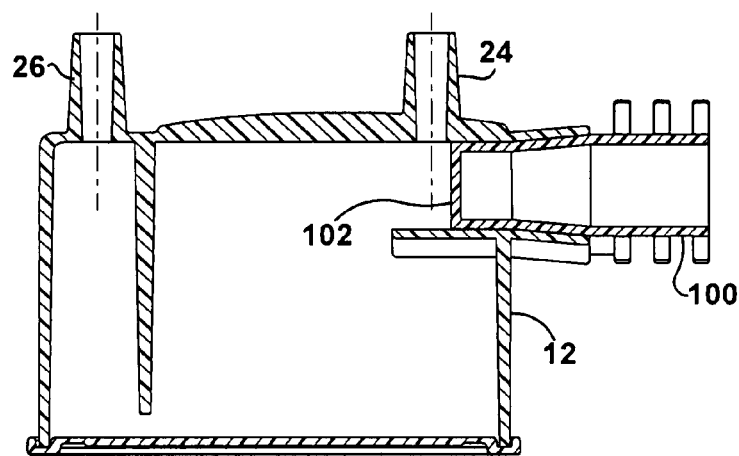
FIG. 5 is a cross-sectional view of the polyp tray of FIG. 1, with a tray plug installed in the collection container.

In the practice of the invention, it is sometimes necessary to initiate or maintain a vacuum in the collection container 12 absent the removable tray 14. FIG. 5 is a cross-sectional view of the collection container 12 with a plug tray 100 installed in the aperture 16. The plug tray 100 includes an vertical end wall 102 sized to seal the aperture 16 in the sidewall of the collection container 12. As such, the plug tray 100 can be used to maintain a vacuum in the collection container prior to the procedure beginning. This technique allows for excessive blood and fluid to be suctioned out of the internal body work site prior to polyp removal. Further, once polyp removal begins, use of the plug tray 102 and removable tray 14 can be alternated to allow for uninterrupted multiple polyp removal. The plug tray is also useful for other purposes, such as for example, maintain a sterile field within the collection container during packaging and shipment to an end user. The plug tray 100 can be installed to maintain a vacuum within the container 12 during shipment provided the ports 24, 26 are also sealed.

Figure 9:
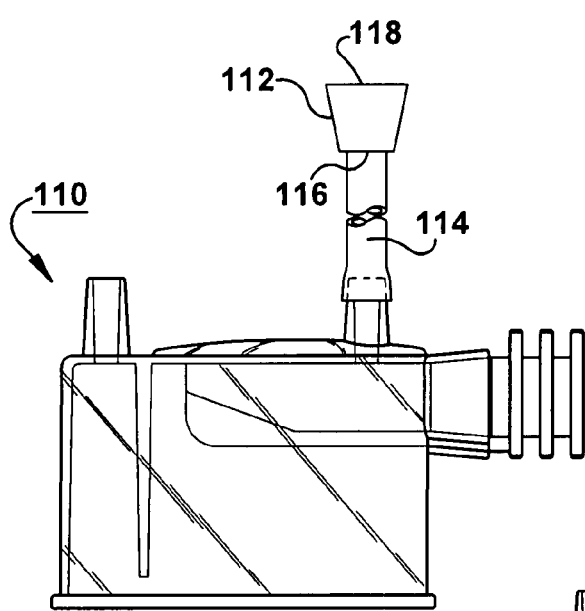
FIG. 9 is a side elevation view of another embodiment of the present invention, showing a polyp trap having a valve on an inlet port.

Another embodiment of the present invention is illustrated in FIG. 9. A polyp trap 110 is shown having a valve 112 in fluid communication with the inlet port 24. The valve has an outlet port 116 connected to an inlet tube 114 to the collection container. The use of this polyp trap 110 allows the inlet tube 114 to be attached directly to the biopsy port inlet of the endoscope by the inlet port 118. An exemplary biopsy valve is described in U.S. patent application Ser. No. 11/137,636, entitled "Irrigating Biopsy Inlet Valve, filed May 25, 2005, which is hereby incorporated by reference in its entirety, to the extent that it is not conflicting with this application.

By connecting the inlet tube 114 to the biopsy port inlet of the endoscope, the polyp has a shorter distance to travel and endures less disruption. Further, the polyp has increased visibility because the polyp travels through the inlet tube 114 attached at a distal and visible portion of the endoscope, as compared to a proximal location behind the physician on the umbilicus. To use the polyp trap 110, the biopsy valve 112 replaces the instrument exchange valve prior to attempting to capture the polyp by suction.

Figure 10:
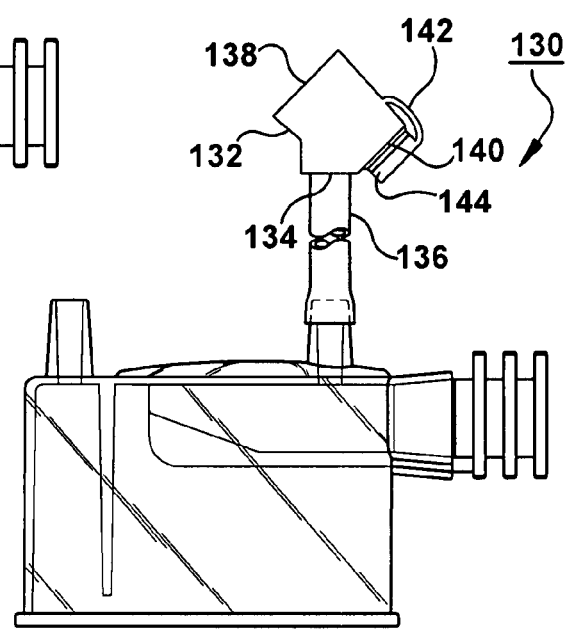
FIG. 10 is a side elevation view of yet another embodiment of the present invention, showing a polyp trap having a valve with instrument accessibility on the inlet port.

FIG. 10 is a side elevation view of yet another embodiment of the present invention, showing a polyp trap 130 having a valve 132 with instrument capability. The valve 132 include a first port 134 for attachment to the inlet tube 136 and a second port 140. A third port 138 is connected to the biopsy port of an endoscope by the inlet port 138. The second port 140 provides access for an instrument to be inserted to the work site, such as for example, forceps to cut the polyp from the gastrointestinal wall. When the physician desires to perform a suction and recover a polyp, the instrument is removed and a cap 144 is used to seal the second port 140. A tether 142 connects the cap 144 to the valve body. This procedure can be repeated without removal of the biopsy valve 132 from the biopsy port inlet of the endoscope.

Figure 11:
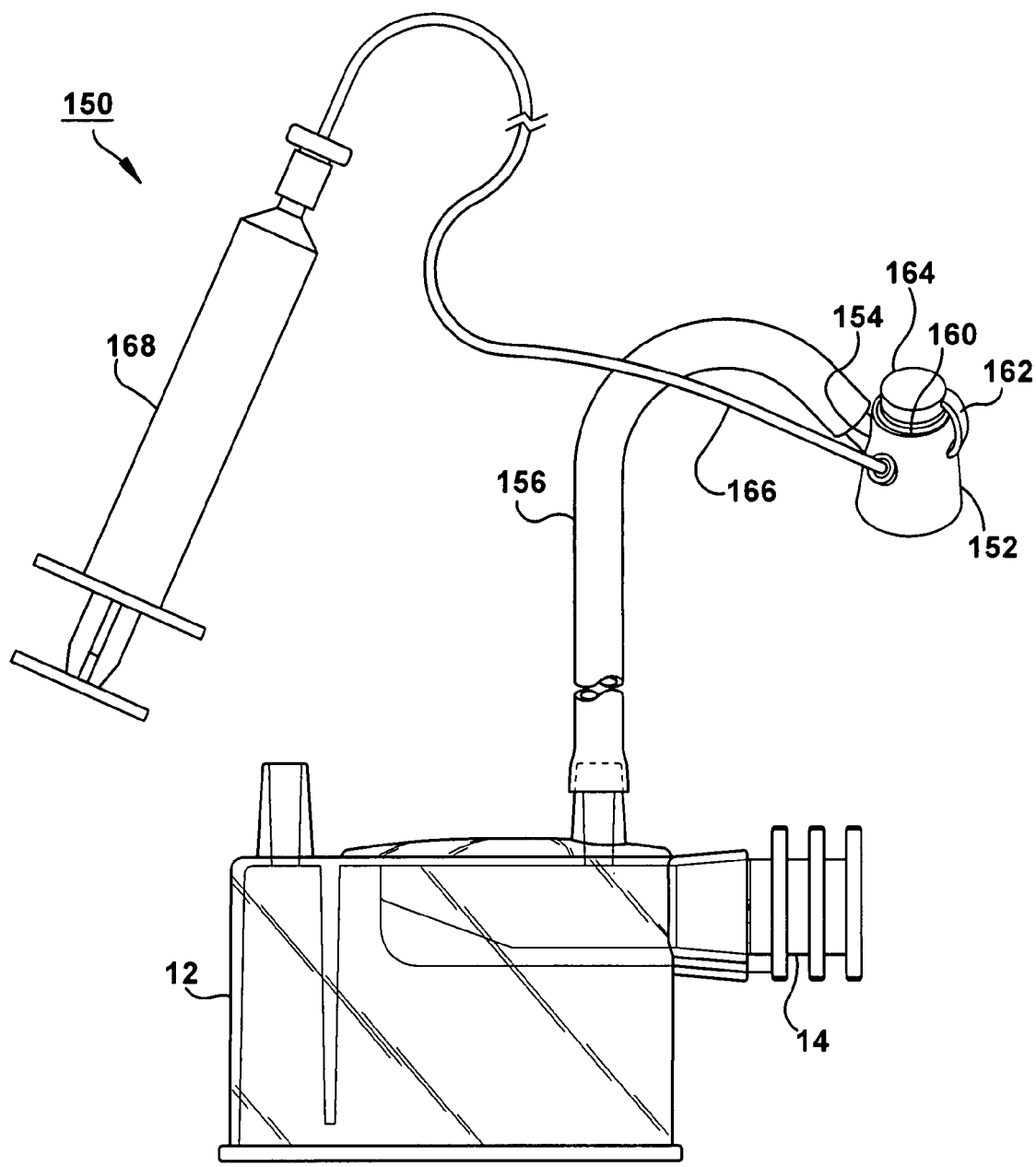
FIG. 11 is a side elevation view of yet another embodiment of the present invention, showing a polyp trap having a valve with irrigation capability on the inlet port.

Another polyp tray 150 is illustrated in FIG. 11. This poly trap 150 includes a valve 152 with irrigation and instrument capability. The valve 152 include a first port 154 for attachment to the inlet tube 156 and a second port 160. An inlet port is connected to the biopsy port of an endoscope. The second port 160 provides access for an instrument to be inserted to the work site, such as for example, forceps. When the physician desires to perform a suction and recover a polyp, the instrument is removed and a cap 164 is used to seal the second port 160. A tether 162 connects the cap 164 to the valve body. This procedure can be repeated without removal of the biopsy valve 152 from the biopsy port inlet of the endoscope. An irrigation line 166 can be used to inject water or other liquids through a needle insert or syringe 168 to irrigate the internal work site. This embodiment offers remote irrigation capability with the poly trap 150 and valve 152 installed on the endoscope. The irrigation line 166 may include a check valve to allow for vacuum of the container 12.

Another feature that can be utilized with any of the aforementioned polyp traps is the addition of an internal light source. Endoscopy suites are frequently dimly lit, and therefore proper visualization of the captured polyp can be challenging. Therefore, the addition of lighting to the device can improve the efficiency of the operation. An embodiment of this concept is illustrated in FIGS. 12 and 13.

A polyp trap 170 including a collection container having an internal cavity 172 sized to contain a light source and a power source is shown in FIG. 12. The location of the cavity 172 could be at alternative locations, such as for example, adjacent or on the base 32. As illustrated in FIG. 12, a light 174 and battery 176 are disposed within the cavity 172. The light 174 and battery 176 can be disposed within the cavity by any technique suitable to avoid displacement during the suction procedure. Other light sources, light locations (inside or outside of the container) and power sources may be used in the practice of this invention.

The lighting system is designed for ease of operation by the user. Further, the system is designed to extend the life of the electrical components. Referring again to FIG. 12, electrical wiring 180 connecting the light and battery to a switch 182 is also shown. The switch 182 is located on an insertion surface 184 contacted by the tray during operation. As such, the light source is activated during a procedure when the tray 12 is inserted. The light assists a user in detecting a polyp on the tray 12.

Figure 13:
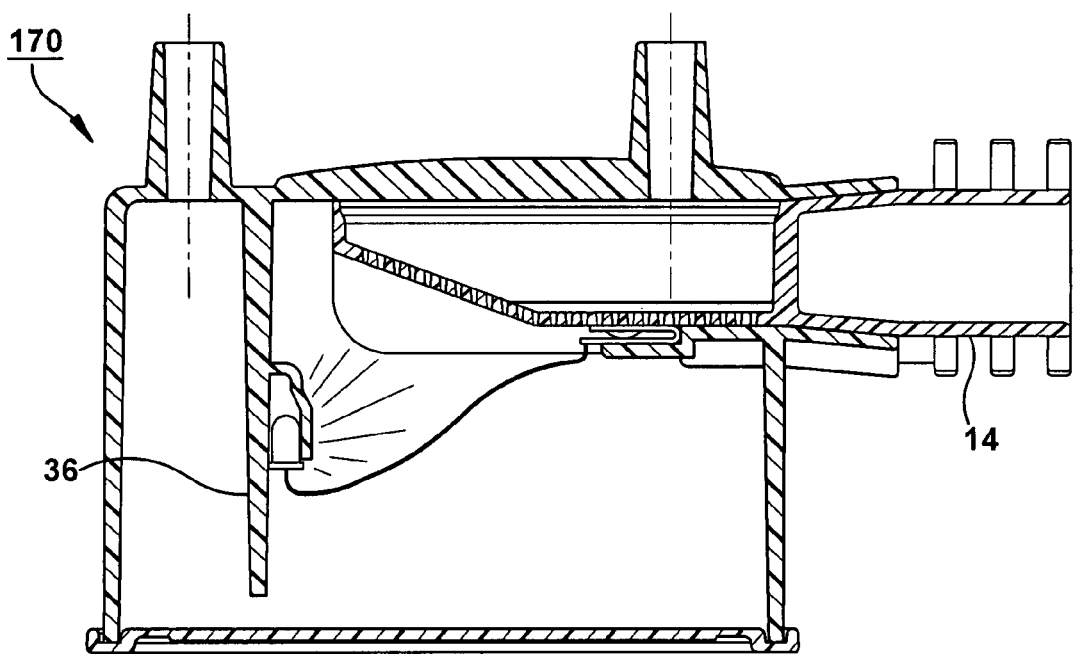
FIG. 13 is a cross-sectional elevation view of the polyp trap of FIG. 12, showing a removable tray in an installed position and a light actuated.

FIG. 13 shows the light 174 actuated upon insertion of the tray 14 into the collection container. When the tray is withdrawn, the light 174 turns off. No other user manipulation beyond movement of the tray 14 is required to operate the light. It should be understood by those with ordinary skill in the art that the placement of the light source, the choice of electrical components and the design of the system itself is for exemplary purposes only and can be greatly varied in the practice of the present invention.

While several embodiments of the invention has been illustrated and described in considerable detail, the present invention is not to be considered limited to the precise constructions disclosed. Various adaptations, modifications and uses of the invention may occur to those skilled in the arts to which the invention relates. It is the intention to cover all such adaptations, modifications and uses falling within the scope or spirit of the claims filed herewith.

What is claimed is:

1. A device for capturing tissue during a medical procedure, the device comprising:
    a) a collection container having an inlet port, at least one sidewall defining an aperture, and an outlet port;
    b) a user graspable and removable tray sized for repetitive manual insertion through said aperture;
    c) an illumination component; and
    d) a dam extending inward from a container sidewall between said inlet port and said outlet port, wherein said dam partially separates said outlet port from said removable tray;
    e) wherein said tray has a perforated surface such that when said tray is inserted into said collection container travel of tissue under suction from said inlet port to said outlet port is inhibited by said tray;
    f) further wherein said tray is contiguous with a surface defining said aperture when in said inserted position.

2. The device of claim 1 wherein said collection container comprises a support platform extending inward from the sidewall aperture.

3. The device of claim 2 wherein at least a portion of said tray rests on said support platform when inserted in said collection container.

4. The device of claim 2 wherein said support platform defines a trough and said tray comprises a protruding ridge sized to engage at least a part of said trough while said tray is inserted in said collection container.

5. The device of claim 1 wherein said collection container comprises a magnifying portion disposed above said tray perforated surface while said tray is inserted in said collection container.

6. The device of claim 1 wherein said collection container is transparent.

7. The device of claim 1 wherein said tray comprises a handle.

8. The device of claim 7 wherein said handle includes a compressible outer surface, such that compressing said handle while said tray is in said collection container releases a seal between said tray and said collection container.

9. The device of claim 1 wherein said tray comprises a basket.

10. The device of claim 9 wherein a bottom surface of said basket has a proximal flat surface and a distal inclined surface.

11. The device of claim 9 wherein said bottom surface of said basket comprises an elongated dividing ridge.

12. The device of claim 1 wherein said tray forms a seal with said surface defining said aperture when fully inserted into said collection container.

13. The device of claim 1 wherein said illumination component is disposed within the collection container.

14. A device for capturing tissue during a medical procedure, the device comprising:
   a) a collection container having a top, an inlet port and an outlet port, sidewalls defining an aperture, and a base, wherein at least a portion of said sidewalls is transparent;
   b) a user graspable and removable tray having a handle and a perforated surface, wherein said tray is sized for partial insertion through said sidewall aperture, wherein said handle remains outside said container;
   c) a light source disposed within said container; and
   d) a dam extending inward from a container sidewall between said inlet port and said outlet port that at least partially separates said container into multiple compartments;
   e) wherein said tray has a perforated surface such that when said tray is inserted into said collection container fluids traveling under suction from said inlet port to said outlet port pass through said tray, and travel of tissue under suction from said inlet port to said outlet port is inhibited by said tray;

further wherein user compression of said handle breaks a suction from said inlet port to said outlet port.

15. The device of claim 14 wherein said top includes a magnifying portion.

16. A device for capturing tissue during a medical procedure, the device comprising:
   a collection container having an inlet port, a sidewall aperture, and an outlet port;
   a user graspable and removable tray sized for movement relative said sidewall aperture between an inserted position within said collection container and a withdrawn position remote from said collection container, wherein said tray in said inserted position is contiguous with a surface defining said aperture; and
   a dam extending inward from a container sidewall between said inlet port and said outlet port that at least partially separates said container into multiple compartments.

17. The device of claim 16 wherein said tray has a perforated surface such that when said tray is inserted into said collection container fluids traveling from said inlet port to said outlet port pass through said tray.

18. A device for capturing tissue during a medical procedure, the device comprising:
   a collection container having an inlet port, a sidewall aperture, and an outlet port;
   a user graspable and removable tray sized for repetitive user movement of said tray relative said sidewall aperture between an inserted position within said collection container and a withdrawn position remote from said collection container, wherein said tray in said inserted position is contiguous with a surface defining said aperture, and said tray disengages from said inserted position by user compression of a non-inserted end said tray; and
   a dam extending inward from a container sidewall between said inlet port and said outlet port, wherein said dam partially separates said outlet port from said removable tray.

* * * * *